United States Patent [19]

Brouillard

[11] 4,029,546

[45] June 14, 1977

[54] COLUMN APPARATUS AND PROCESS FOR IMMOBILIZED ENZYME REACTIONS

[75] Inventor: Robert Ernest Brouillard, Cedar Rapids, Iowa

[73] Assignee: Penick & Ford, Limited, Cedar Rapids, Iowa

[22] Filed: Mar. 29, 1976

[21] Appl. No.: 671,063

[52] U.S. Cl. .......................... 195/31 R; 195/31 F; 195/63; 195/68; 195/116; 195/139; 195/DIG. 11

[51] Int. Cl.² .................. C12D 13/02; C12B 1/00; C07G 7/02

[58] Field of Search ............. 195/63, 68, DIG. 11, 195/31 R, 31 F, 127, 139, 116

[56] References Cited

UNITED STATES PATENTS

| | | | |
|---|---|---|---|
| 3,919,048 | 11/1975 | Dahlmans et al. | 195/63 |
| 3,944,470 | 3/1976 | Diehl et al. | 195/63 |
| 3,960,663 | 6/1976 | Tamura et al. | 195/31 F |

Primary Examiner—Lionel M. Shapiro
Attorney, Agent, or Firm—Tilton, Fallon, Lungmus, Chestnut & Hill

[57] ABSTRACT

A column apparatus and process is provided for immobilized enzyme reactions using a bed of regenerated sponge material chemically modified to incorporate enzyme-immobilizing groups. The sponge material selected for use in column apparatus has a flow of direction length of 2 to 5 feet or more, a density of less than 1 gram for each 18 cc. of bed volume (e.g. 1 g./20–70 cc. bed vol.), and a water flow porosity such that over 0.5 (preferably over 1.0) gal. water/min./ft.² flows through the bed. The apparatus and process can be used with a wide variety of enzymes, but has particular applicability to the enzymatic conversion of starch hydrolysates. Starch-derived sugar syrups having D.E.'s of 40 to 97 can be produced. Also, isomerization of glucose syrups can be carried out to produce a syrup of enhanced sweetness, comprising a mixture of glucose and fructose.

21 Claims, 2 Drawing Figures

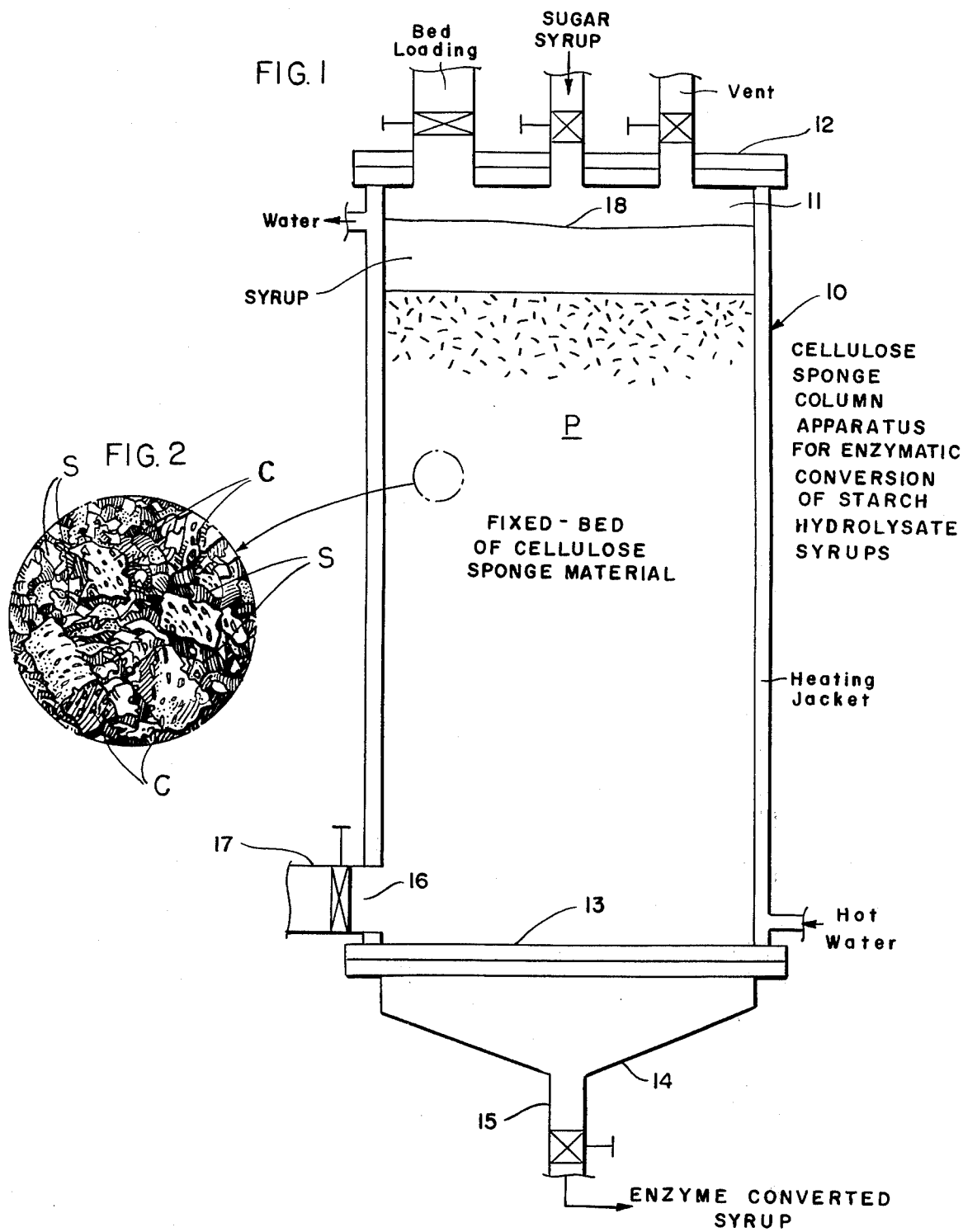

COLUMN APPARATUS AND PROCESS FOR IMMOBILIZED ENZYME REACTIONS

BACKGROUND AND PRIOR ART

The properties of ion exchange celluloses have been studied for chromatographic separations and immobilization of enzymes. See, for example, Guthrie et al, *Ind. J Eng. Chem.*, 52, 915–916 (Nov. 1960); Barker et al, *Carbohyd. Res.*, 8, 491–497 (1968); and Wilson et al, *Biotech. J Bioeng.*, XI, 349–361. Natural celluloses modified to incorporate cationic groups, such as tertiary amine or quaternary ammonium groups, are available commercially in microgranular and fibrous forms. The di- and tri-ethylaminoethylated celluloses are referred to, respectively, as DEAE-cellulose and TEAE-cellulose, while the cationic derivative of cellulose prepared by reaction with epichlorohydrin and triethanolamine is known as ECTAEOLA-cellulose. Companies which are understood to have produced cationic celluloses for commercial use include Brown Company, New York, N.Y., W. & R. Balston, Ltd., Kent, England, and Servi Co., Heidelberg, Germany.

As far as is known, however, the only commercial application of enzymes immobilized on an ion exchange cellulose has been in connnection with the partial conversion of starch-derived glucose to fructose, thereby obtaining a syrup of increased sweetness. For this purpose, glucose isomerase enzyme is bound to DEAE-cellulose (or similar cationic cellulose), and the glucose syrup is passed through a series of very thin beds of the isomerase-containing cellulose. See, Schnyder, B. J., "Continuous Isomerization of Glucose to Fructose on a Commercial Basis", *Die Starke*, 26, 409–412 (1974); and Thompson et al U.S. Pat. No. 3,788,945, granted Jan. 29, 1974. This technology, as applied commercially by Standard Brands Incorporated and A.E. Staley & Company, involves the use of contact beds of 1 to 5 inches in thickness. This is necessary so that the pressure drop across each bed is small and the compaction of the bed is minimal. But because of the thinness of the beds, in order to avoid the effects of substrate channeling, it is essential to employ a series of such beds. Consequently, fixed-bed columns, such as are used for processes involving ion-exchange resins, cannot be employed. Instead, pressure leaf filters are used. The glucose isomerase bound to the cellulose carrier is pumped as an aqueous slurry through the pressure leaf filter in such a manner as to cover each leaf evenly with a thin layer of the cellulose material. As disclosed in U.S. Pat. No. 3,788,945, the depth to width ratio of the beds is preferably limited to from about 0.02 to 0.05.

Because of the expense and inconvenience of carrying out glucose isomerization in pressure leaf filters, the corn syrup industry has been actively searching for alternative processes where the glucose isomerase enzyme can be immobilized on a material usable in commercial-size fixed bed columns. Such column materials must effectively immobilize the enzyme; be chemically and physically stable, resisting disintegration under conditions of use; and being sufficiently porous while minimizing channeling effects, so that there is adequate and uniform contacting but with no excessive pressure drop across the bed. Some microorganisms which produce isomerase contain this enzyme in the cell, and the enzyme is bound therein, or can be bound by a heat treatment. For example, a column material can be prepared for Arthrobacter cells. One process is described in U.S. Pat. No. 3,821,086. Such natural column material shows considerable promise, and provides advantages over the use of shallow beds of cellulose-immobilized isomerase. However, the need is great for a column material of general utility, which can be used for immobilizing soluble isomerase, as well as other soluble enzymes, such as those used for the conversion of starch oligosaccharides to dextrose and maltose. Such a column material could be used to immobilize alpha amylase, glucoamylase, or mixtures thereof, for commercial production of corn starch-derived syrups having D.E.'s from 40 to 97.

In particular, to minimize capitol investment, increase plant capacity and reduce production costs, there has been a manifest need for a column process to produce intermediate D.E. corn syrups, such as the syrups now produced by enzymatic hydrolysis of corn starch to obtain syrups having a D.E. in the range of about 40 to 70. As far as is known, all present commercial processes for producing this type of syrup utilize a final stage batch enzyme treatment in which the soluble enzymes are dissolved in the syrup. This is a one-time enzyme use. Usually, the final stage involves treatment simultaneously with an alpha-amylase and a glucoamylase. Therefore it would be desirable to provide a column material to which a mixture of these enzymes can be chemically bonded and immobilized therein. Such a column material and column apparatus would also have many other applications, and could be used, in general, wherever batch enzyme treatments of substrates with soluble enzymes are now used.

SUMMARY OF INVENTION

The novel column apparatus and process for immobilized enzyme reactions of this invention is based in part on the discovery that an efficient and relatively inexpensive column material for immobilizing enzymes can be prepared from regenerated cellulose in sponge form. It is the physical properties of the selected cellulose sponge material, which primarily characterize the novelty of the column apparatus and process of this invention. Although regenerated celluloses are known to have substantially lower molecular weights and degrees of polymerization than native cellulose, it has been found that regenerated cellulose in sponge form can be readily modified by known chemical processes to incorporate effective amounts of enzyme-immobilizing groups. In fact, it is one of the surprising aspects of the present invention that all of the chemistry needed to practice the invention has been well-known for many years, being described in detail in the chemical literature and prior patents for application to natural cellulose. For example, as has been done commercially for native cellulose, regenerated cellulose sponge material can be chemically modified by known processes to produce DEAE-, TEAE-, ECTEOLA-sponge cellulose.

The regenerated cellulose sponge can be used as a starting material for the purpose of the present invention and is readily available, being manufactured by a number of companies for sale as household or industrial cleaning sponges. Moreover, the scrap or waste from the preparation of cellulose cleaning sponges can be used. One type of such waste material is known as "D-slab". It consists of the trim ends of the cellulose sponge sheets as formed before cutting into sponge blocks. Heretofore, this trim end material has had relatively little commercial value, although it has had some use, such as filling for inexpensive pillows and similar upholstering uses. It is therefore unexpected that D-slab trim sponge wastes can be used for immobilized enzyme columns.

The preparation and characteristics of cellulose sponge material for use in the column apparatus and immobilized enzyme reaction processes of this invention will subsequently be described in detail. However, certain important features may be indicated here. By selecting and processing the cellulose sponge material so that it has a density under conditions of use of less than a certain maximum, and preferably within a specified range, the sponge material may be employed in deep beds of the kind conventionally used for fixed-bed columns. Moreover, high flow-through rates can be employed without substantial liquid pressure drop across the beds. As will be appreciated, therefore, the resulting column apparatus and immobilized enzyme reaction process represents a great improvement over the prior art of thin-bed enzyme-immobilizing cellulose materials.

As far as is known, it is broadly new to employ cellulose sponge in a column apparatus or process for immobilized enzyme reactions. With respect to a column material in sponge form, a recent U.S. Pat. No. (3,919,048) describes the use of ground natural sponge for enzyme immobilization, and proposes the natural sponge as a column filling. However, natural sponge differs both chemically and physically from regenerated cellulose sponge. Natural sponge is formed of spongin, which consists mainly of protein. In large pieces, it has large openings forming channels therethrough. When ground it is as dense as powdered natural cellulose.

Experiments have also been conducted of other natural proteinaceous materials for insolubilization of enzymes, namely collagen powder and collagen sponge. Silman et al, *Biopolymers*, 4, 441–448 (1966). The purpose was to study the effect on papain, and no suggestion is made to use collagen sponge for fixed-bed column-type enzyme reactions.

It is therefore quite surprising and unexpected that cellulose sponge, which is available as a scrap material, and which, as far as is known, has not heretofore been used in any enzymatic processes, can be employed as the key element of a column apparatus and process for immobilized enzyme reactions.

THE DRAWING

The accompanying drawing in FIG. 1 illustrates a fixed-bed column apparatus utilizing a bed of regenerated cellulose sponge material in accordance with the present invention, the apparatus being illustrated in conjunction with a preferred process, namely, the enzymatic conversion of syrups.

FIG. 2 is a greatly enlarged view of the material of the bed, which, in the illustration given, consists of a mixture of rectilinear pieces of sponge and sponge shreads.

DETAILED DESCRIPTION

Cellulose sponge material for use in practicing the present invention is available commercially, and include the cellulose sponge scrap known commercially as "D-slab" trim ends. When the sheets of cellulose sponge are molded in the forming boxes, it is necessary to trim the ends of the sheets before they are cut into sponge blocks for sale as cleaning sponges. However, there is a variation in the density of cellulose sponge material as supplied commercially, both in the form in which it is shipped, and after being wet with water to expand the sponge to its maximum volume. Some sponge material is compressed for compactness in marketing, and in that form may have a density as great as 1 gram (dry basis) of sponge material per 3 to 4 cubic centimeters (cc.). When such sponges are wet and fully expanded, their volume increases to a stable volume of about 25 to 32 cc. per g. Other cellulose sponge material as shipped by the manufacturer have a density in the range of 13 to 16 cc/g., and on being wet with water expand to a maximum stable volume having a density as low as 1 g./25 cc. As will be discussed below, selecting a sponge material which provides the proper density under conditions of column use is important. If necessary, cellulose sponge materials can be prepared to a specified density; the porosity and thereby the density, being controlable by the relative proportion of water-soluble salt mixed with the viscose prior to the molding operation.

The process for the manufacture of cellulose sponges parallels the manufacture of rayon by the viscose process but does not require the more elaborate finishing steps. Instead of being pumped to the spinning machine, the viscose is mixed with a minor proportion of a fibrous reinforcing material consisting of cotton, hemp, ramie, flax, jute, coco, staple fiber, etc. (either in a natural or alkali swollen state), and a crystalline pore-forming material capable of inducing coagulation of the viscose on heating, usually a hydrated salt with a low melting point such as Glauber's salt, $Na_2SO_4 \cdot 10 H_2O$. The content of fibrous material is usually about 5 to 10% by weight basis on the cellulose content.

The mixture of viscose, fibrous reinforcing material and crystalline pore-forming material is then formed and the cellulose coagulated and regenerated. The finished sponge is washed free of salts and other contaminants. Modern processes incorporate colored pigments into the viscose/fiber/crystalline mixture, and generally also add softening agents, usually polyhydric alcohols, and bleaching agents such as hydrogen peroxide to the regenerating baths to improve the physical properties of the sponge and increase the saleability of the product. Sodium sulfate and carbon disulfide are recovered in the process. The fibrous content of the regenerated cellulose sponge is desirable but not essential, for the purposes of this invention. The physical stability of the cellulose sponge material for column use, particularly when the material is employed in subdivided condition, as preferred, is believed to be improved by the content of fibrous reinforcing material. Water soluble additives, such as softening agents, are removed by washing the sponge material with water prior to use for enzyme immobilization. Such washing can be carried out either before the sponge material is charged to the columns, or the washing can be carried out in the columns.

Detailed procedures for the manufacture of cellulose sponges are set in the patent literature, such as the patents of E. I. duPont de Nemours & Company, a major commercial producer of cellulose sponges. See, for example, U.S. Pat. Nos. 2,133,810 and 3,284,229. DuPont cellulose sponge as sold commercially for cleaning sponges, or the D-slab trim ends of such DuPont sponge material, has been found to have excellent physical properties for the purposes of the present invention. Another suitable sponge material is sold commercially by a division of General Mills, Tonawanda, N.Y., as the "O-Cel-O" cellulose sponge. For such sponge materials, hemp is a particularly suitable reinforcing fiber, and may be incorporated in an amount of about 6 to 8% by weight hemp (dry basis) based on the weight of the regenerated cellulose. As indicated above, however, although the incorporation of a minor amount of a fibrous reinforcing material in the cellulose sponge material is desirable, the amount and kind of reinforcing material can be varied widely. Desirably, however, the reinforcing material is in the range of 5 to 10% by weight (dry basis) based on the regenerated cellulose, and is itself a cellulosic material, so that its fibrous form is not affected by enzymes other than cellulases.

While the cellulose sponge material can be employed in the form of large sheets, pads, or blocks, it is preferably used in a subdivided form, which facilitates the filling and uniform packing of a fixed-bed column. For example, D-slab cellulose sponge scrap can be shredded to produce a mixture of shreds having a size in the range of 0.263 to 0.525 Tyler Equivalent Screen Size. Oversized material is not objectionable, that is pieces of material having a size greater than 1.050 screen size (Tyler), but it will usually be desirable to separate the ultra-fine material, which may result from the shredding operation, namely, the particles having a screen size less than 0.185 (Tyler). Alternatively, or additionally, the cellulose scrap or other cellulose sponge starting material can be cut into small generally rectilinear chunks or blocks having approximate average dimensions of from $0.25 \times 0.25 \times 0.25$ inches up to at least $0.75 \times 0.75 \times 0.75$ inches. These sizes are not critical, but simply advantageous. Further, it has been found desirable to mix the sponge shreds with the sponge blocks, such as from 80 to 120 parts by weight of the sponge shreds per 100 parts of the small blocks.

The objective is to produce a column packing material having a density under conditions of use such that less than 1 gram of sponge material (dry basis) fills 18 cubic centimeters of bed volume or more. For example, the density of the sponge material can be such that 1 gram of the material (dry basis) fills from 20 to 70 cubic centimeters of bed volume. For certain processes, densities within the range of 1 gram of sponge material (dry basis) per at least 25 cc., such as 30 to 60 cc. of bed volume are preferred. The sponge material need not be compressed in the column bed, but can be allowed to occupy its natural stable volume after being thoroughly wet with water. Once expanded by water-wetting, the volume of the cellulose sponge material does not change appreciably. Further, the contacting operations are carried out with aqueous solutions, so that during contacting, the volume of the sponge material per unit weight remains substantially unchanged. Since the sponge material is modified, as will be subsequently described, to incorporate enzyme immobilizing groups therein, it will be understood that the density will be on the basis of the modified sponge material, such as sponge material in cationic form, but that all water soluble components of the sponge as supplied by the manufacturer, have been removed, and are not included in calculating the column density.

With cellulose sponge beds of the character described, there will be little or no pressure drop across the beds due to the flow resistance of the sponge material. Deep beds can therefore be employed. Even if a series of beds are used, the bed depths will be at least 2 feet in the direction of flow, and preferably at least 5 feet. The maximum bed depth or height, where the column extends vertically, can extend for as much as 40 to 50 feet, although typical columns may range from 5 to 20 feet in the direction of flow. The beds may be used in column apparatus having round, square, or rectilinear cross-sections. Usually the cross-sectional area wil be substantially uniform throughout the length of the column. There is no limit on the lateral extent of the beds, although usually the diameter or lateral extents of the beds will range from about 5 to 15 feet. A typical column apparatus, therefore, might comprise a vertically-extending column, for either upflow or downflow contacting, having a height sufficient that a bed can be incorporated therein with some head room thereabove, having a height of from 8 to 20 feet, and a diameter of from 5 to 10 feet.

Columns prepared as described, will have a high degree of liquid porosity while avoiding channeling effects. More specifically, water can be flowed through beds of over 10 feet in height at flow rates in excess of 0.5 and preferably in excess of 1.0 gallon per minute per square foot of bed cross-sectional area. If the cross-section of the bed varies the smallest cross-section is used to determine flow rate. When an enzyme conversion is being conducted in the column, the rate of flow is only limited by the contact time necessary to achieve the desired conversion. There will be substantially no liquid pressure drop across the bed due to the flow resistance of the sponge material. For example, the solution to be contacted can be pumped into the top of a column having a head space above the fixed-bed of cellulose sponge material, at a rate maintaining a liquid level above the top of the bed. The outflow rate from the bottom of the bed can be controlled correspondingly, so that the liquid, in effect, percolates through the bed without any pump pressure being required. The difference in static head between the top and the bottom of the bed, will be due to the height of the liquid in the column, and not to the resistance of the cellulose bed. Alternatively, the solution to be contacted can be pumped into the bottom of the column flowing upwardly through the bed, the head space above the bed being maintained substantially full of the contacted liquid. The outflow will be controlled in relation to the in-flow, and the pump pressure required for the operation being only that necessary to move the liquid against its own static head, and not due to the resistance of the sponge material itself. As will be understood, the beds can also be used so that the flow direction is horizontal, although more commonly, the beds will be used in vertically-extending columns with a downwardly direction of flow.

In preparing the column material, it has been found undesirable to grind the cellulose sponge to a very fine state of subdivision, where the sponge structure is largely eliminated. As the extent of subdivision increases to that of a fine powder, the density of the ground sponge material increases until it is comparable to that of present commercial cationic cellulose powders, such as DEAE-cellulose prepared from natural cellulose. In one test, ground cellulose sponge was found to have a density after wetting and full expansion corresponding to 1 gram of sponge material per 18 cc. The material was still much more permeable to water than natural cellulose powder, but the porosity for use in deep bed columns was not as satisfactory as where the sponge material under conditions of use has a density (dry basis) of less than 20 cc. per gram of sponge material. In general, column-fill densities under conditions of use of less than 18 cc. per gram (dry basis) of sponge material are undesirable.

For the purpose of the present invention, the cellulose sponge material is chemically modified to incorporate an effective amount of enzyme-immobilizing groups. In general, reagents bonding immobilizing groups to the regenerated cellulose chains through ether linkages can be employed. Cationic groups are preferred but enzyme-immobilizing anionic groups are also known, and could be used for some purposes. A wide variety of cationic etherifying agents can be employed, such as those described in U.S. Pat. Nos. 3,823,133 and 3,809,605. Further, where required to chemically stabilize the cellulose, cross-linking procedures can be used to permit a higher degree of substitution to be obtained, thereby increasing the capacity of the regenerated cellulose. Suitable procedures for this purpose are described in the literature, for example, in Guthrie et al, *Ind. J Engr. Chem.*, 52, 915-917 (1960). As is known in the art, tertiary amine and quaternary ammonium groups are particularly effective for immobilizing enzymes. The regenerated cellulose may therefore be modified to incorporate the di- and triethylaminoethyl groups, providing DEAE-regenerated cellulose and TEAE-regenerated cellulose, respectively. The regenerated cellulose can be reacted according to known procedures with epichlorohydrin and triethanolamine to form ECTOLA-regenerated cellulose. It will be understood that all of these derivatives are formed while the regenerated cellulose material remains in sponge form.

Where the cellulose sponge material is to be subdivided in preparing the column fill, this can be done first, the undersized fines removed by screening, and the grated subdivided sponge material washed with water to remove any soluble constituents. The subdivided sponge material can then be derivatized, using the procedures and reagents indicated above. A variety of such reagents and procedures are also illustrated in the following example. Since the chemistry involved in the reaction procedures are well-known, it is not believed it will be necessary to further discuss them herein.

Contrary to what might have been expected, it has not been found necessary to incorporate high levels of the enzyme-immobilizing groups in the cellulose sponge capacity in column use. In general, where cationic nitrogen groups are introduced as the immobilizing groups, the number of such groups can correspond from 0.2 to 2.0 percent added nitrogen by weight nitrogen based on the dry weight of the cationic sponge material. Moreover, for many purposes, adequate capacity is obtained where the cationic nitrogen groups, such as tertiary amine groups or quaternary ammonium groups, are present in the cellulose sponge material in an amount corresponding to only 0.3 to 1.0 percent added nitrogen based on the dry weight of the cationic sponge material.

The column apparatus and column process of this invention for immobilized enzyme reactions is applicable to all enzymes which are immobilized by the functional groups and which do not attack or degrade the cellulose structure of the sponge. In general, enzymes as a class are adsorbed and immobilized by cationic nitrogen groups, such as tertiary amine or quaternary ammonium groups. Cellulase enzymes are not desirable, since their primary action is digest cellulose. Cross-linking of the cellulose can increase its resistance to cellulolytic attack, and therefore enzymes containing trace amounts of cellulases may be employed. However, preferably, cellulose sponge material is not employed for reactions requiring the presence of immobilized cellulase, and, also, it is preferred that the enzymes applied to the column be substantially free of cellulase.

For enzymatic conversion of glucose, and mixtures of glucose with oligo-saccharides derived from natural starch, such as corn starch, the enzymes will be those which have heretofore been employed for such purposes, particularly alpha-amylase, glucoamylase, or mixtures of these enzymes. For conversions of glucose syrups to mixtures of glucose and fructose, glucose isomerase can be employed. For this purpose, a high D.E. feed stock is preferred, such as a starch derived glucose solution having a D.E. of 93 to 97, indicating that it is composed of large amounts of dextrose. For producing intermediate D.E. syrups from corn starch or other starch materials, the feed stock can be a starch derived mixture of glucose and oligosaccharides having a D.E. in the range of 15 to 45. For example, a mixture of alpha-amylase and glucoamylase enzymes can be applied to the cellulose sponge material, and employed with a feed stock of the character described to produce products having D.E.'s in the range of 42 to 70. These are important commercial products which are now produced entirely by batch-type enzyme conversions involving one-time use of the enzymes. With the process of the present invention, the useful life of the enzymes may be greatly extended, being usable for converting at least 10 to 20 times the amount of substrate to the intermediate D.E. corn syrup of commerce.

Other enzymes which can be used in the process and apparatus of this invention include trypsin, papain, chymotrypsin, lactase, urease, acylase, catalase, penicillin-amidase, beta-amylase, lipase, glucose oxidase, protease, gelatinase, hemicellulase, pectinase, lysozyme, pepsin, etc.

The following Experimental Examples are illustrative and provide further information about the enzyme-immobilizing cellulose sponge material prepared for use in the apparatus and process of this invention. The starting material was cellulose sponge or sponge scrap (D-slab) produced by E. I. duPont, Wilmington, DEL. The fiber content of the cellulose sponge material was not specifically determined, but is believed to comprise about 6 to 8 percent by weight of hemp fibers based on the dry weight of the regenerated cellulose. This material was found to be identical in properties to duPont cellulose sponges purchased in retail stores. In general, the duPont cellulose sponge as received has a density of about 1 gram per 13-16 cc. of material. On thorough wetting with water, the cellulose sponge, in the form of sheets or blocks expands to a stable density averaging 1 gram per 28 cc. When the cellulose sponge material is subdivided, such as by shredding, the density can be further decreased. Such shredded material on being thoroughly wet with water, expanded to a stable density averaging about 51 cc. per gram (dry basis). It will be understood that the density after expansion by water wetting corresponds with the density expected of the material under ordinary conditions of use. The density, however, is related to the dry weight of the cellulose sponge material, which includes the regenerated cellulose, the fibrous reinforcing material, and the added enzyme-immobilizing groups, but excludes water-soluble substances that are removed from the sponge cellulose material before it is used in columns for immobilized enzyme reactions.

EXPERIMENTAL EXAMPLES

EXAMPLE 1

Derivatives of regenerated cellulose sponge (DuPont Cellulose Sponge) were prepared by reaction with cationizing reagents according to the following general procedure: The sponge was shredded to produce thin pieces ("shreds") of an average size of around 0.25 to 0.75 inches in length. The sponge shreds were washed in hot water, dried, and resuspended in water containing an amount of salt from a strong acid and a strong base representing supersaturation and a strong base consisting of an alkali metal hydroxide was added. The cationizing reagent was then added and reaction continued with stirring at an elevated temperature for about 2 hours. After this, the cationized cellulose sponge was recovered by neutralizing to about pH 4 ;1 with mineral acid, filtered, washed with water and dried to equilibrium moisture in an air oven.

Applying this procedure to a specific example 20 grams (0.125 mole) of washed, shredded cellulose sponge was suspended in 970 grams of water containing 580 grams of sodium sulfate. An amount of 12 grams of 50% sodium hydroxide solution (0.15 mole) was added followed by 10.3 grams (0.06 mole) of diethylamino-ethylchloride hydrochloride (DEC). The mixture was stirred at 45° C for 130 to 190 minutes. Thereafter, the mixture was adjusted to pH 4 with hydrochloric acid, held for 1 hour, filtered, and washed by resuspending in 6 successive 2-liter portions of water to remove the salts of reaction and the sodium sulfate present during the reaction. The final product was dried at 80° C. and allowed to equilibrate at room temperature to obtain diethylaminoethyl (DEAE) sponge cellulose, usable as a column material for immobilized enzyme reactions. Nitrogen was determined on the product to determine the amount added as shown in Table 1.

Also shown in Table 1 are the results of other experiments wherein the mole ratio of the reagent to the regenerated cellulose of the sponge was varied as well as the amount of alkali catalyst added, on a dry cellulose basis (d.b. cellulose).

Table 1

| Run | Mole Ratio DEC/ Cellulose | Reaction in Minutes | % NaOH on d.b. Cellulose | % Nitrogen Added |
|---|---|---|---|---|
| A | 1:2 | 120 | 30 | 1.36 |
| B | 1:2 | 130 | 60 | 1.20 |
| C | 1:2 | 130 | 30 | 1.61 |
| D | 1:5 | 190 | 30 | 0.85 |
| E | 1:1 | 130 | 60 | 2.04 |

The nitrogen added is a measure of the DEAE groups bonded to the sponge cellulose, which are available for enzyme immobilization.

EXAMPLE 2

Using the procedure described in Example 1, and following the details of Run A, a derivative of a cellulose sponge column material was prepared using as a reagent, 4-chloro-2-butenyl trimethylammonium chloride, except that the produce was adjusted to pH 1, held for 1 hour, and washed as before. After recovery in the manner previously described, the amount of nitrgogen added was found to be 0.66%. This is a measure of the cationic groups which are trimethyl ammonium butanoyl-2-cellulose ether groups in chloride form. The resulting cationic sponge can be used as a column material for immobilized enzyme reactions.

EXAMPLE 3

Using the procedure of Example 1, and following the details of Run A, a derivative of cellulose sponge was prepared using as a reagent 2,3-epoxypropyl trimethylammonium bromide. After recovery in the manner previously described, the amount of nitrogen added was found to be 0.24%. This is a measure of the cationic groups which are 2-hydroxy-propyl trimethyl ammonium cellulose ether groups in bromide form. The resulting cationic sponge can be used as a column material for immobilized enzyme reactions.

EXAMPLE 4

A variant of the reagent described in Example 3 was reacted in the same manner, using 3-chloro-2-hydroxypropyl trimethylammonium chloride. The recovered product was found to contain 0.35% added nitrogen. This is a measure of the cationic groups which are 2-hydroxypropyl-trimethyl ammonium cellulose ether groups in chloride form. The resulting cationic sponge can be used as a column material for immobilized enzyme reactions.

EXAMPLE 5

Using the procedure described in Example 1, and following the details of Run A, a derivative of the regenerated cellulose sponge was prepared using as a reagent, 4-bromobutyl trimethylammonium bromide. After recovery in the manner previously described, the amount of nitrogen added was found to be 0.45%. This is a measure of the cationic groups which are butyl trimethyl ammonium cellulose ether groups in bromide form. The resulting cationic sponge can be used as a column material for immobilized enzyme reactions.

EXAMPLE 6

Cellulose sponge shreds cationized according to Run A in Example 1 with DEC to contain 1.26% added nitrogen, as DEAE cellulose sponge, was treated with an enzyme solution to cause the enzyme to be adsorbed onto the cationic sponge.

An amount of 10 grams d.b. of cationic sponge was mixed with 10 grams of glucoamylase (Diazyme L-100, Miles Laboratories, Elkhart, Ind.) in ion-exchanged water at room temperature for four hours, and filtered, yielding a mixture containing 770 IGU of enzyme activity. The sponge was separated from the liquid by filtering and analysis showed an activity of 35.4 IGU/gram. IGU = an immobilized glucoamylase unit and is the amount of enzyme which will catalyze, under the assay conditions, the production of one gram of glucose in 1 hour. Assay conditions constitute use of a solution of 30% aqueous maltodextrin solids maintained at pH 4.2 and 60° C. for 1 hour. Enzyme activity is measured by calculating the increase in glucose concentration.

Six grams of sponge containing glucoamylase was wetted with water, placed in a 1-inch diameter column, and 30% solids concentration syrup at 35% dextrose equivalent (D.E.; Standard Analytical Methods, Corn Refiners Association, Method E-26) flowed through the column at a rate of 4 ml./minute at pH 4.2 and 138°

F. The D.E. of the effluent syrup was maintained at 45%. After 7 days an amount of 14,870 grams of syrup (dry solids basis) had been passed through the column.

EXAMPLE 7

Cellulose sponge shreds cationized according to Run A in Example 1 with DEC to contain 0.33% added nitrogen, as DEAE cellulose sponge, was treated with Diazyme L-100 enzyme solution as in Example 6 and found on analysis to contain an activity of 24.3 IGU per gram.

Eight grams of the sponge containing enzyme was placed in a 1-inch diameter column and room temperature. A 30% solids ion exchange syrup at 36% D.E. was flowed into the column at pH 4.5. The column was gradually heated to 140° F. and the effluent syrup flowing at a rate of 6 ml./minute yielded 62% D.E.

As flow was continued, the percent D.E. gradually dropped to 51% D.E. after 7200 grams by dry substance produce had been collected. The flow was then reduced to 3 ml./minute and the percent D.E. recovered to 60.

The column was briefly exposed to 152° F. which inactivated the enzyme present. An additional amount of a glucoamylase (G-zyme; Enzyme Development Corp., New York, N.Y.) was added to the column by adding it to the feed syrup and flowing it onto the column. The column was adjusted to 140° F. and 36% D.E. ion exchanged syrup flowed through the column at 3 ml./minute until a quantity of 60% D.E. syrup equivalent to 42,000 grams dry substance syrup had been produced over a 24-day period.

EXAMPLE 8

This example shows the capability of a column of cationized cellulose sponge to contain a mixture of enzymes, and vary the sugar balance of the resulting syrup product. Ten grams of cellulose sponge shreds cationized with DEC according to Run A in Example 1 to contain 0.85% nitrogen, as DEAE cellulose sponge, was treated with a blend of 1.16 grams of a fungal α-amylase (Asperzyme; Enzyme Development Corp.) and 0.60 gram of G-zyme (See Example 7). The enzymes were dissolved in 42% D.E. syrup at 30% solids and flowed through the column several times before beginning a flow of syrup at pH 5.5 at a rate of 3 ml./minute. The effluent syrup was 64.1% D.E., and showed on analysis, 40.3% dextrose and 30.6% maltose.

After 7 days, a quantity of 10,318 grams dry substance syrup had been produced with the D.E. gradually falling to 48% at the same flow rate.

EXAMPLE 9

This example shows a different method of mixing the enzyme with the cationized sponge.

Six grams of DEAE sponge material (identical to that in Example 8) were treated with the same quantity of Asperzyme and G-zyme (see Examples 7 and 8) and allowed to mix over night in 42% D.E. syrup at 35% solids concentration and pH 5.5 at 130° F. The column was then filled with ion exchanged syrup at 44% D.E. and at a flow rate of 4 ml./minute the effluent syrup was 66% D.E. Analysis showed a sugar balance of 47.6% dextrose and 22.3% maltose.

After observing that the pH of the effluent syrup began to drift downward to 4.7, the feed syrup was switched to carbon refined syrup. Hereafter, the pH of the effluent syrup was the same as the influent syrup. At a flow rate of 3.4 ml./minute at pH 5.5, the syrup produced was 62.2% D.E., and the sugar balance was found to be 42.6% dextrose and 22.5% maltose.

EXAMPLE 10

This example shows the effect of varying the influent D.E. of a syrup and its conversion by a fungal alpha amylase. Eight grams of cationized regenerated cellulose sponge shreds (DEAE) containing 0.48% added nitrogen was treated with 2 grams of Asperzyme (see Example 8), a fungal alpha amylase dissolved in water. The mixture was added to a column and 35% D.E. carbon refined syrup containing 0.01% sodium bisulfite at pH 5.5 and 35% solids was flowed onto the column at room temperature. The column temperature was raised to 130° F.

The effluent syrup collected at a flow rate of 3 ml./minute was 50.7% D.E. and had a sugar balance of 20.2% dextrose and 37.7 maltose.

After a period of time, the influent syrup was changed to 19.4% D.E., all other parameters being the same. The effluent syrup had a sugar balance of 4.8% dextrose and 40% maltose.

EXAMPLE 11

This example is similar to Example 8 except that the cationized (DEAE) sponge material contained 0.38% added nitrogen. The same ratio of Asperzyme and G-zyme (see Examples 7 and 8) was added in the manner of Example 10. Influent syrup at 43.5% D.E., 35% solids concentration, pH 5.5, and containing 0.01% sodium bisulfite was flowed through the column at 130° F. at a rate of 3 ml./minute.

Effluent syrup contained 63.6% D.E. and had a sugar balance of 35.5% dextrose and 31.5% maltose.

EXAMPLE 12

Regenerated cellulose sponge cationized with DEC (see Example 1) to contain 0.85% added nitrogen was treated with an enzyme solution to cause the enzyme to be absorbed onto the cationic sponge.

An amount of 1 gram dry basis (d.b.) of cationic sponge was mixed with 1 gram of a purified invertase (Convertit; Wallerstein Company, Morton Grove, Ill.), in ion exchanged water at room temperature for 4 hours. The sponge was separated from the liquid by filtration and washed on the filter with ion exchanged water to remove unbound enzyme.

One-half gram d.b. of sponge containing invertase was mixed with 50 ml. of 10% sucrose solution at pH 5.0 and 55° C. for 30 minutes yielding 86% invert sugar, demonstrating the presence of invertase activity in the sponge.

EXAMPLE 13

One gram of DEAE cellulose sponge identical to that in Example 12 was mixed with 1 gram Glucose Oxidase (Worthington Biochemical Corporation, Freehold, N.J. in ion exchanged water to produce a sponge containing glucose oxidase according to the procedure described in Example 12.

One-half gram d.b. of sponge containing glucose oxidase was mixed with 50 ml. of 1% glucose solution at pH 7.0 and 37° C. After 3 hours, 95% of the glucose had been oxidized as indicated by loss of reducing power of the solution. This result demonstrates the presence of glucose oxidase in the sponge.

EXAMPLE 14

One gram of DEAE-cellulose sponge identical to that in Example 12 was mixed with 1 gram Urease (Jack Bean, double strength, J. T. Bake Chemical Company, Phillipsburg, N.J.) in ion exchanged water to produce a sponge containing Urease according to the procedure described in Example 12.

One-half gram d.b. of sponge containing Urease was mixed with 0.1 gram urea in 250 ml ion exchanged water at pH 6.5 in a stoppered Kjeldahl flask at ambient temperature for 1 hour. A nitrogen determination (Urea and Ammonical Nitrogen; Methods of Analysis, 11th ed., AOAC, Method 7.027) showed complete decomposition of the urea. This result demonstrates the presence of urease activity in the sponge.

EXAMPLE 15

One gram of DEAE sponge identical to that in Example 12 was mixed with a cell-free extract of glucose isomerase (obtained from Arthrobacter cells, NRRL 3728) to produce a sponge containing glucose isomerase, according to the procedure described in Example 12.

A glucose isomerase assay of the sponge containing glucose isomerase showed an activity of $2.3 \times 10^{-3}$ units/gram d.b. sponge, where one unit is defined as the amount of enzyme which catalyzes the formation of 1 gram of fructose per minute under the following conditions: 60° C., 1.67 molar glucose, pH 7.75, and 0.4 molar magnesium. This result demonstrates that the sponge contains immobilized glucose isomerase. This sponge can be used for column conversion of glucose to fructose.

EXAMPLE 16

One gram of DEAE sponge identical to that in Example 12 was mixed with 1 gram Catalase (Miles Laboratories, Elkhart, Ind.) in ion exchanged water to produce a sponge containing catalase, according to the procedure described in Example 12.

When one-half gram d.b. of sponge containing catalase was mixed with 50 ml. of 1% hydrogen peroxide, the peroxide was immediately decomposed. This result demonstrates the presence of catalase activity in the sponge. The sponge can be used in a column for continuous decomposition of $H_2O_2$ in an aqueous medium.

EXAMPLE 17

One gram of DEAE sponge identical to that in Example 12 was mixed with 0.5 gram Trypsin (Miles Laboratories, Elkhart, Ind.) in ion exchanged water to produce a sponge containing trypsin according to the procedure described in Example 12.

One-half gram d.b. of sponge containing trypsin was mixed with 50 ml. of 2% casein solution at pH 7.0 and 37° C. After 30 minutes, the sponge was removed from the solution and trichloroacetic acid was added to precipitate the protein. A Kjeldahl nitrogen determination after filtration to remove the precipitate showed that enzyme activity was retained by the sponge. The sponge can be used as column material for continuous treatment of soluble protein, the protein being proteolyzed by the immobilized trypsin.

EXAMPLE 18

This example describes the preparation of a cationized cross-linked cellulose sponge.

A DEAE cellulose sponge derivative was prepared as in Example 1 using DEC, and following the details of Run A. Then the reaction slurry was adjusted to pH 1 and 20% by weight of formaldehyde (based on d.b. cellulose of the sponge material and the formaldehyde) was added and the mixture stirred for 1 hour. Thereafter, the product was adjusted to pH 3.9 and washed as previously described. It contained 1.3% added nitrogen, as DEAE groups.

An amount of 8 grams of the resulting cross-linked sponge material was contacted with 1.16 grams of Asperzyme and 0.6 gram of G-zyme (see Examples 7 and 8) dissolved in water. The mixture was added to a column and 37% D.E. carbon refined syrup containing 0.01% sodium bisulfite at pH 5.5 and 35% solids was flowed into the column at room temperature. The temperature was raised to 130° F. and the flow rate adjusted to about 3.0 ml./minute.

The effluent syrup was 66.6% D.E. and had a sugar balance of 47.6% dextrose and 29.2% maltose.

EXAMPLE 19

A cationized cellulose sponge derivative was prepared as in Example 18 using DEC, except that 100% by weight of formaldehyde was reacted for 1 hour. The product was adjusted to pH 4.0 and washed until no odor of formaldehyde was detectable. The product contained 1.16% added nitrogen, and was usable as a cationic column material for immobilized enzyme reactions.

For example, an amount of 40 grams of the resulting cross-linked cationic sponge material was contacted with 5.8 grams of Asperzyme and 3.0 grams of G-zyme (see Examples 7 and 8) dissolved in water. The mixture was added to a column and 37% D.E. carbon refined syrup containing 0.01% sodium bisulfite at pH 5.4 and 35% solids was flowed into the column at room temperature. The temperature was raised to 130° F. and the flow rate adjusted to 11 ml./minute. The effluent syrup had a D.E. of 67%.

EXAMPLE 20

The cationic cellulose sponge material may be used in columns in several forms, in the foregoing examples the sponge was in the form of small pieces which resulted from a shredding operation. An alternative procedure involves the use of plugs cut from the sponge mass, which are slightly smaller than the internal column diameter. The plugs are allowed to swell within the column.

By way of specific example, cylindrical plugs (height 1 foot, diameter 15/16 inch) of regenerated cellulose sponge were derivatized as described in Example 1 and dried. Ten of these plugs were inserted into a column (1 × 12 inch) and water down-flowed through the column until the sponge had been thoroughly wet and expanded. It then formed a tight seal against the walls and the height was 11 inches.

Five grams of Diazyme L-100 (see Example 6) in 50 cc. of water was added to the column. When all of the enzyme solution had been added, flow was stopped and the system maintained at 30° C. for 2 hours. Then corn syrup was added to the column, as described in Example 6. Similar results were obtained.

During the course of column operation, the flow rate was varied. D.E. of the effluent varied from 40 to 95, depending on the flow rate.

The density of the enzyme containing sponge in the column may be varied considerably by applying pressure to the top of the sponge layer with a screen, which can either prevent upward expansion when plugs are used; or can substantially reduce the apparent volume when shredded sponge is used, the screen being moved downwardly to compress the shredded material. Using the latter technique, it is feasible to densify the bed, as required, to reduce channeling. Such bed compaction does not appear to cause back-pressure or flow difficulties.

OTHER EXAMPLES

In addition to the foregoing, other procedures for preparing enzyme-immobilizing celluloses can be used. These include the following:

EXAMPLE 21

A carboxymethylchloro-S-triazinyl derivative of regenerated cellulose sponge can be prepared according to Example 1 of U.S. Pat. No. 3,278,392. It will absorb urease from an aqueous solution for immobilization thereof. When the enzyme containing sponge is put in a column and a urea solution is down-flowed the effluent will contain substantially no urea.

EXAMPLE 22

Similar enzyme absorption and immobilization results can be obtained when regenerated cellulose sponge is made cationic with a diazotized anthranilic ester (U.S. Pat. No. 3,647,630), or a p-diazophenoxyhydroxy propyl ether (U.S. Pat. No. 3,702,804), or a bromoacetyl derivative (U.S. Pat. No. 3,278,392), or by cyanogen bromide activation [*Biotechnology and Bioengineering*, Vol. XIV, p. 1039 (1972)]. The foregoing citations illustrate applicable reaction procedures.

EXAMPLE 23

A carbonate of regenerated cellulose sponge can be prepared from ethyl chloroformate, as described in Example 1 of U.S. Pat. No. 3,810,821. The anionic sponge will absorb anyloglucosidase from a water solution which cannot be removed by washing. The enzyme containing sponge, when put in a down-flow column can be used to give D.E.'s ranging from 60 to over 90 when the input corn syrup substrate has a D.E. of 34–38.

COMMERCIAL EXAMPLES

The following examples are intended to illustrate preferred commercial practice, as presently envisioned.

EXAMPLE 24

A column apparatus is employed of the kind conventionally used with ion exchange resins. Such an apparatus is illustrated diagrammatically in FIG. 1. The vertically-extending column 10 provides internally a space for receiving the fixed-bed of cellulose sponge packing P. Above the material there is provided an open head space 11. The column 10 is provided with a heating jacket, as indicated in FIG. 1, through which hot water can be circulated for maintaining a selected temperature during the enzyme reaction. The top or cover of the column 12, which may be removable, is provided with a series of connections, the larger one on the left, as indicated, being used for loading the cellulose sponge material into the bed, the center one for supplying the solution to be converted, such as starch hydrolysate, and the one on the right to be used as an air vent. All of these inlets may be provided with suitable valves, as shown. The bottom of the bed is supported on a screen 13, which retains the cellulose material of the bed, while permitting liquid flow therethrough into the tapered bottom portion 14 which converges to outlet 15. The outflow through 15 is controlled by means of a valve, as indicated. Immediately above screen 13 on one side of the column, there is provided a clean-out opening 16 which communicates with a removal pipe 17 through a valve, as shown. With this arrangement when the cellulose sponge material is in sub-divided condition, as preferred, it can be pumped into the column in the form of a water slurry, the bed loading inlet at the top being used. After repeated use of the cellulose sponge bed, it may be desirable to remove the bed material, and replace it with a new cellulose sponge bed. This can be done by introducing water through the bed loading and/or syrup inlets at the top, the valve being opened on outlet pipe 17, and the bed material being pumped out as as slurry through pipe 17.

One advantageous form of the column material is illustrated in FIG. 2. It consists of a mixture of sponge shreads and small blocks or chunks, which are roughly cubical or rectilinear. The shreds preferably have a size such that they pass through a number 0.525 screen while being retained on a number 0.263 screen (Tyler). The "cubed" material can have an average size of ¼ to ½ inches in each dimension. The blocks or chunks may be somewhat irregular in shape, since the sponge shreds fill the spaces between the larger pieces. This is indicated in FIG. 2 where the larger pieces are designated by the letter C, and the intervening shread by the letter S. Desirable proportions range from 50 to 60 parts by weight of the shredded material to 30 to 40 parts of the "cubed" material.

In the use of the apparatus of FIG. 1, such as for conversion of a syrup with an appropriate enzyme, the syrup is pumped into the head space 11 at the top of the column, and a level is maintained therein above the top of the bed of cellulose sponge material, as indicated at 18. The valve on outlet line 15 is opened to permit outflow at substantially the same rate as the inflow, the column 10 being maintained full of the aqueous syrup to be converted. In this operation, the syrup flows downwardly through the bed at a rate, which is sufficient to achieve the level of conversion desired. The height and diameter of the bed may be varied, as required, for the particular process. In the processes described in the following examples, the bed of cellulose sponge material, for example, may have a height of about 12 feet and a diameter of about 8 feet.

EXAMPLE 25

Batches of 26 pounds of regenerated cellulose sponge (duPont) in the form of approximate cubes varying in size from 0.75 inches are suspended in 500 pounds of water at 120° F. in a 175-gallon ribbon blender. After agitating for 20 minutes, the water is drained from the system. The washing process is repeated three times without removing the sponge from the blender to provide a sponge free of impurities.

To the washed wet sponge is then added 440 gallons of water, 125 pounds of anhydrous sodium sulfate, 12.5 pounds of 47% sodium hydroxide, and 3.9 pounds of DEC.HCI. Additions are made while agitating and in the order given. The stirred mixture is agitated for 1.5 hours while maintaining the temperature at 50° C. The pH of the mixture is then adjusted to pH 4 with hydrochloric acid and agitated for one-half hour. The mixture is drained and then washed six times by adding water, agitating for 20 minutes, draining, and repeating the process.

The wet sponge is then dried at 38° C. This provides the derivatized cellulose sponge in cube form. The nitrogen content of the product is 0.60%.

The shredded form of the derivatized sponge is prepared by grinding the cube form above in a Fitz mill using a 2-mesh screen.

One hundred thirty-six pounds of homogeneous mixture of 65 parts cubes and 35 parts of the shreds is introduced into a 3 × 12 column (FIG. 1). Water is then introduced to swell the sponge and allow an excess of 1 foot of water above the bed. The cellulose bed is 6 feet in depth.

A solution of 20.5 pounds of Fungamyl (Novo) in 850 pounds water is then circulated through the column for 2 hours. Thereafter, a solution of 10.24 pounds dry basis of glucoamylase (G-zyme, Enzyme Development) is added to the water and is circulated through the column for 2 hours.

Filtered acid hydrolyzed corn starch hydrolyzate (syrup) with an average D.E. of 36–38 is then added to the top of the column. The syrup temperature is 130° F. and the pH adjusted to 5.5.

When column operation has stabilized, it produces 65 D.E. syrup containing 36% dextrose and 35% maltose at a flow rate of 4.5 gallons per minute.

EXAMPLE 26

The procedure of Example 25 is followed using only G-zyme (25 pounds) for attachment to the regenerated cellulose sponge. Other conditions are identical except that the pH is maintained at 4.0–4.5 and the temperature at 140° F. The syrup produced has a D.E. of 95.

EXAMPLE 27

The procedure of Example 26 is followed using cell-free enzyme from streptomyces ATCC 21175 prepared as described in Example 1 of U.S. Pat. No. 3,788,945. When used in a column operation with a 6 bed depth and a substrate syrup of 95 D.E. at pH 8, a product containing 42% fructose at commercially acceptable flow rates can be produced.

I claim:

1. Column apparatus for immobilized enzyme reactions, including column means providing a flow-through reaction chamber between the liquid inlet and outlet ends thereof, said reaction chamber extending for several feet in the direction of liquid flow, wherein the improvement comprises: a bed of regenerated cellulose sponge material in said reaction chamber for liquid passage therethrough, the regenerated cellulose of said material having been chemically modified to incorporate an effective amount of enzyme-immobilizing groups, said bed of sponge material being characterized by having (a) a flow direction length of at least 2 feet, (b) a density under conditions of use of less than 1 gram of said sponge material (dry basis) per each 18 cubic centimeters of bed volume, and (c) a water flow porosity such that over 0.5 gallons of water per minute per square foot of bed cross-section will flow therethrough without substantial liquid pressure drop due to flow resistance of the sponge bed.

2. The improved column apparatus of claim 1 wherein said reaction chamber and said bed of sponge material have a flow direction length of at least 5 feet.

3. The improved column apparatus of claim 1 wherein said sponge bed under conditions of use has a density of less than 1 gram of said sponge material (dry basis) per each 20 to 70 cubic centimeters of bed volume.

4. The improved column apparatus of claim 1 wherein said sponge bed has a water flow porosity such that more than 1.0 gallon of water per minute per square foot of bed cross-section will flow therethrough without substantial liquid pressure drop across the length of the bed due to the flow resistance of the sponge bed.

5. Column apparatus for immobilized enzyme reactions, including vertically-extending column means providing a flow-through reaction chamber between the vertically-spaced liquid inlet and outlets thereof, said reaction chamber having a vertical extent in the direction of liquid flow of more than 5 feet, wherein the improvement comprises: a bed of regenerated cellulose sponge material disposed in said reaction chamber for liquid passage therethrough the regenerated cellulose of said material having been chemically modified to incorporate an effective amount of enzyme-immobilizing groups, said sponge bed being characterized by (a) a vertical depth between said inlet and outlets of at least 5 feet, (b) a density under conditions of use of less than 1 gram of said sponge material (dry basis) per each 20 cubic centimeters of bed volume, and (c) a liquid flow porosity such that more than 1.0 gallons of water per minute per square cubic foot of bed cross-section flow therethrough without significant liquid pressure drop across the bed in the direction of flow due to the flow resistance of the sponge bed.

6. The improved column apparatus of claim 5 in which the enzyme-immobilizing groups chemically bonded to said regenerated cellulose are cationic nitrogen groups, the number of said groups on the basis of added nitrogen corresponding to 0.2 to 2.0 percent by weight nitrogen based on the dry weight of said cationic sponge material.

7. Column apparatus for immobilized enzyme reactions, including column means providing a flow-through reaction chamber between the liquid inlet and outlet ends thereof, said reaction chamber extending for several feet in the in direction of liquid flow, wherein the improvement comprises: a bed of regenerated cellulose sponge material in said reaction chamber for liquid passage therethrough, the regenerated cellulose of said material containing chemically bonded cationic nitrogen groups effective for enzyme-immobilization, said groups being selected from tertiary amine groups and quaternary ammonium groups, said groups being present in an amount corresponding to 0.3 to 1.0 percent added nitrogen based on the dry weight of the cationic sponge material, said sponge bed having a flow direction length of at least 5 feet, and a density under conditions of use such that 1 gram of said cationic sponge material (dry basis) fills from 20 to 70 cubic centimeters of bed volume.

8. Column apparatus for immobilized enzyme reactions, including vertically-extending column means providing a flow-through reaction chamber between vertically-spaced liquid inlet and outlet means, said reaction chamber extending for more than 5 feet in the vertical direction of liquid flow, wherein the improvement comprises: a liquid-permeable bed of cationic regenerated cellulose sponge material in said reaction chamber, the cationic groups of said sponge material being of the kind and being present in an amount throughout said bed effective for immobilizing enzymes in said bed, said sponge bed having a vertical depth in the direction of flow of over 5 feet, and a liquid flow porosity such that more than 0.5 gallons of water per minute per square foot of bed cross-section will flow therethrough without substantial liquid pressure drop across said bed in the direction of flow due to the flow resistance of the sponge bed.

9. The improved column apparatus of claim 8 in which said sponge bed under conditions of use has a density such that 1 gram of said cationic sponge material (dry basis) fills from 30 to 60 cubic centimeters of bed volume.

10. The improved column apparatus of claim 7 in which said sponge bed has a liquid flow porosity such that more than 1.0 gallons of water per minute per square foot of bed cross-section will flow therethrough without substantial liquid pressure drop across the bed in the direction of flow due to the flow resistance of the bed.

11. The improved column apparatus of claim 7 in which said cationic nitrogen groups are selected from the class consisting of tertiary amine groups and quaternary ammonium groups, and the sponge material of said bed contains an amount of said groups corresponding to 0.3 to 1.0 percent by weight of added nitrogen based on the dry weight of the cationic sponge material.

12. The process for reacting a water-soluble enzyme-convertible substance with an enzyme other than cellulase, in which a water solution of the substance is passed through a porous bed of material containing immobilized therein at least one enzyme for the reaction, wherein the improvement comprises employing as said bed a regenerated cellulose sponge material which has been chemically modified to incorporate an effective amount of enzyme-immobilizing groups, said bed of sponge material having a flow direction length of at least 2 feet and a density under conditions of use of less than 1 gram of said sponge material (dry basis) per each 18 cubic centimeters of bed volume, and passing said water solution through said bed at a rate of over 0.5 gallon of solution per minute per square foot of bed cross-section.

13. The process of claim 12 in which said bed of sponge material has a flow direction length of at least 5 feet, and a density under conditions of use of less than 1 gram of said sponge material (dry basis) per each 25 cubic centimeters of bed volume.

14. The process for reacting a water-soluble enzyme-convertible substance with an enzyme other than cellulase, in which a water solution of the substance is passed through a porous bed of material containing immobilized therein at least one enzyme for the reaction, wherein the improvement comprises employing as said bed a regenerated cellulose sponge material which has been chemically modified to incorporate an effective amount of enzyme-immobilizing groups, said bed of sponge material having a flow direction length of at least 5 feet and a density under conditions of use such that 1 gram of said sponge material (dry basis) fills from 20 to 70 cubic centimeters of bed volume, and passing said solution through said bed at a rate of more than 1.0 gallon of solution per minute per cubic foot of bed volume.

15. The process of claim 14 in which said sponge bed under conditions of use has a density such that 1 gram of said sponge material (dry basis) fills from 30 to 60 cubic centimeters of bed volume.

16. The process of claim 14 in which the enzyme-immobilizing groups chemically bonded to said regenerated cellulose are cationic nitrogen groups, the number of said groups on the basis of added nitrogen corresponding to 0.2 to 2.0 percent by weight nitrogen based on the dry weight of the cationic sponge material.

17. The process for reacting a water-soluble enzyme-convertible substance with an enzyme other than cellulase, in which a water solution of the substance is passed through a porous bed of material containing immobilized therein at least one enzyme for the reaction, wherein the improvement comprises employing as said bed a regenerated cellulose sponge material which has been chemically modified to incorporate an effective amount of enzyme-immobilizing groups, the regenerated cellulose of said material containing chemically bonded cationic nitrogen groups effective for enzyme-immobilization, said groups being selected from tertiary amine groups and quaternary ammonium groups, said groups being present in an amount corresponding to 0.3 to 1.0 percent added nitrogen based on the dry weight of the cationic sponge material, said sponge bed having a flow direction length of at least 5 feet and a density under conditions of use such that 1 gram of said cationic sponge material (dry basis) fills from 20 to 70 cubic centimeters of bed volume, and passing said solution through said bed at a rate of over 1.0 gallon of solution per minute per square foot of bed cross-section.

18. The process for enzymatically converting a sugar substrate selected from the group consisting of glucose, oligosaccharides derived from starch, and mixtures of glucose and said oligosaccharides, in which a water solution of said sugar substrate is passed through a porous bed of material containing immobilized therein at least one enzyme for said conversion selected from the group consisting of alphaamylase, glucoamylase, and glucose isomerase, wherein the improvement comprises employing in said bed a regenerated cellulose sponge material which has been chemically modified to incorporate an effective amount of enzyme-immobilizing groups therein, said bed of sponge material having a flow direction length of at least 5 feet and a density under conditions of use of less than 1 gram of said sponge material (dry basis) per each 20 cubic centimeters of bed volume, and passing said sugar solution through said bed at a rate of over 0.5 gallon of solution per minute per square foot of bed cross-section.

19. The process of claim 18 in which said bed of sponge material has a flow direction length of at least 5 feet and a density under conditions of use such that 1 gram of said sponge material (dry basis) fills from 30 to 60 cubic centimeters of bed volume, and in which said solution is passed through said bed at a rate of over 1.0 gallon of solution per minute per square foot of bed cross-section.

20. The process of claim 18 in which the enzyme-immobilizing groups chemically bonded to said regenerated cellulose are cationic nitrogen groups, the number of said groups on the basis of added nitrogen corresponding to 0.2 and 2.0 percent by weight nitrogen based on the dry weight of said cationic sponge material.

21. The process of claim 18 in which said enzyme-immobilizing groups chemically bonded to said regenerated cellulose are cationic nitrogen groups selected from tertiary amine groups and quaternary ammonium groups, said groups being present in an amount corresponding to 0.3 to 1.0 percent added nitrogen based on the dry weight of the cationic sponge material, and said sponge bed having a density such that 1 gram of said cationic sponge material (dry basis) fills from 30 to 60 cubic centimeters of bed volume.

* * * * *